United States Patent [19]

Savage

[11] Patent Number: 5,014,217

[45] Date of Patent: May 7, 1991

[54] APPARATUS AND METHOD FOR AUTOMATICALLY IDENTIFYING CHEMICAL SPECIES WITHIN A PLASMA REACTOR ENVIRONMENT

[75] Inventor: Richard N. Savage, Livermore, Calif.

[73] Assignee: S C Technology, Inc., Livermore, Calif.

[21] Appl. No.: 308,570

[22] Filed: Feb. 9, 1989

[51] Int. Cl.$^5$ ............... H01L 21/306; C23F 1/02; G06F 15/20
[52] U.S. Cl. .................... 364/498; 364/552; 364/550; 156/626; 204/192.33
[58] Field of Search ............ 364/498, 499, 552, 550, 364/468, 500; 156/345, 626, 627; 204/192.13, 192.25, 192.15, 192.33; 250/281, 288; 73/863, 863.01

[56] References Cited

U.S. PATENT DOCUMENTS

| | | | |
|---|---|---|---|
| 3,434,545 | 3/1969 | Bombardieri | 166/307 |
| 3,831,030 | 8/1974 | Wrobel et al. | 250/339 |
| 3,986,761 | 10/1976 | Redington | 316/17 |
| 4,008,388 | 2/1977 | McLafferty et al. | 364/498 |
| 4,301,369 | 11/1981 | Matsuo et al. | 250/423 R |
| 4,309,385 | 1/1982 | Harada et al. | 422/83 |
| 4,365,303 | 12/1982 | Hannah et al. | 364/498 |
| 4,493,745 | 1/1985 | Chen et al. | 156/626 |
| 4,584,886 | 4/1986 | Matsunaga et al. | 73/863 |
| 4,620,058 | 10/1986 | Winterling et al. | 136/258 |
| 4,620,284 | 10/1986 | Schnell et al. | 364/498 |
| 4,637,938 | 1/1987 | Lee et al. | 427/53.1 |
| 4,676,868 | 6/1987 | Riley et al. | 156/643 |
| 4,754,141 | 6/1988 | Mindock | 250/343 |
| 4,847,792 | 7/1989 | Barna et al. | 364/552 |

OTHER PUBLICATIONS

Savage, Dr. Richard N. and Lettire, Kevin C., "Characterizing Reactive Plasma Chemistries," Microelectronic Manufacturing and Testing, (Nov. 1986).

Savage, Richard N., "Applications of Optical Emission Spectroscopy to Semiconductor Processing," Spectroscopy, vol. 2 (No. 8), pp. 40–42, (1987).

UTI Instruments Company, "The Intelligent Way to Control the Environment Inside Your Processes," ISS-325 Intelligent Sampling Systems, (Sunnyvale Calif. 1984).

Linda Powell, Computer Search and Indentification of Infrared Spectra by Correlation Techniques, Indiana University, Bloomington, Ind., (1977).

Primary Examiner—Parshotam S. Lall
Assistant Examiner—Ellis B. Ramirez
Attorney, Agent, or Firm—Flehr, Hohbach, Test, Albritton & Herbert

[57] ABSTRACT

A method and apparatus to control the plasma environment in a semiconductor or thin-film fabrication chamber. The apparatus and method include a means for measuring an optical emission spectrum of the chemical species in the plasma and a library containing a multiplicity of predefined spectral patterns. A processor automatically correlates the spectrum with the predefined spectral patterns in the library, and yields a correlation value for all the correlations. A subset of the predefined spectral patterns based upon the highest correlation values are selected and used to identify the chemical species and abundances thereof in the plasma. A comparator compares the subset with a target set of plasma species and abundances and a control signal generator generates a control signal in response to the comparison to control the chamber environment. In a preferred embodiment, the control signal controls the plasma environment in the reactor chamber when said subset differs from said target set by a predefined amount.

19 Claims, 5 Drawing Sheets

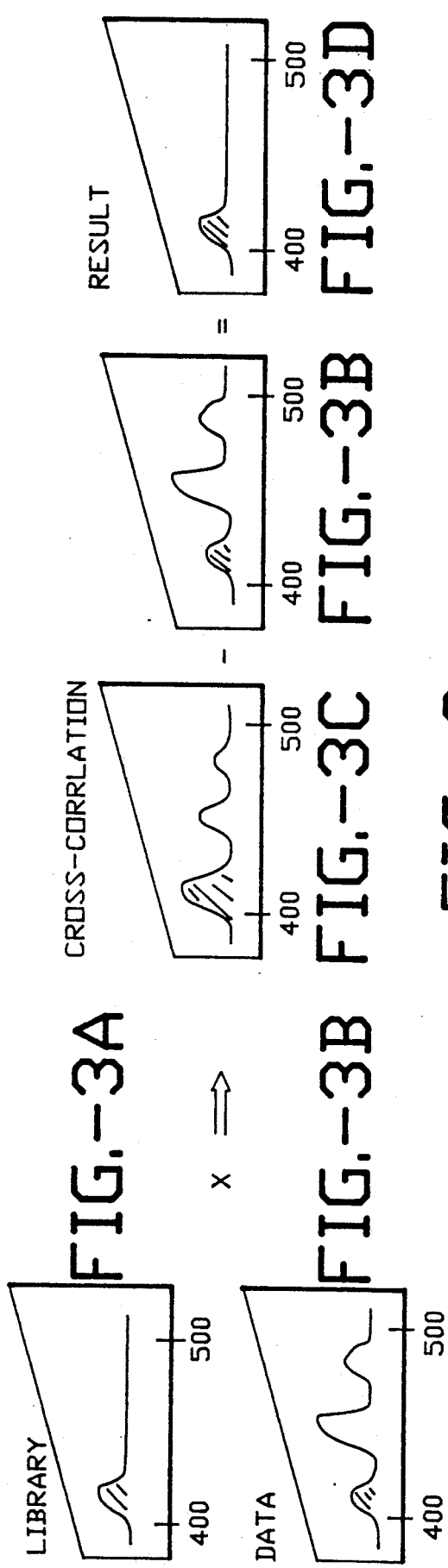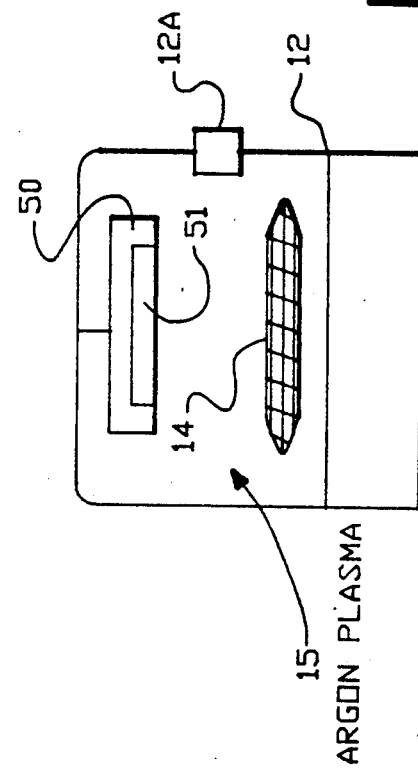

GOLD SPUTTERING
FIG.-5
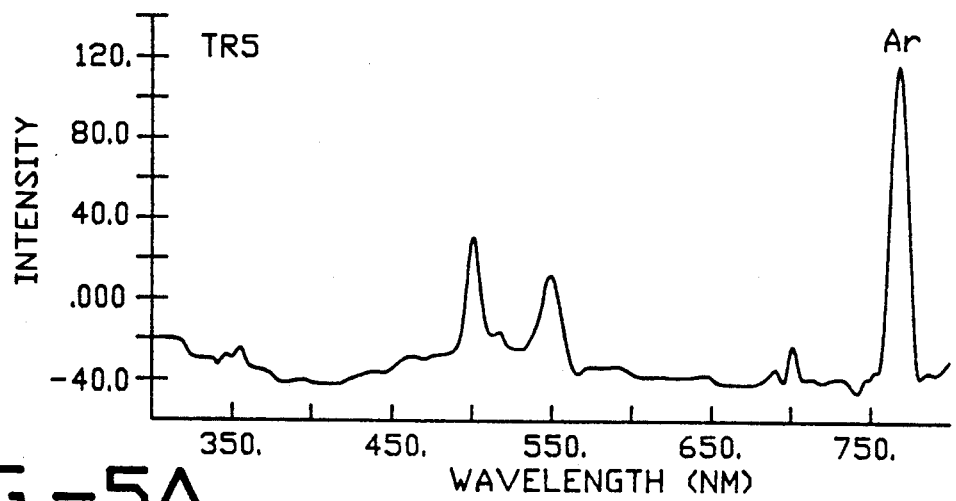
FIG.-5A
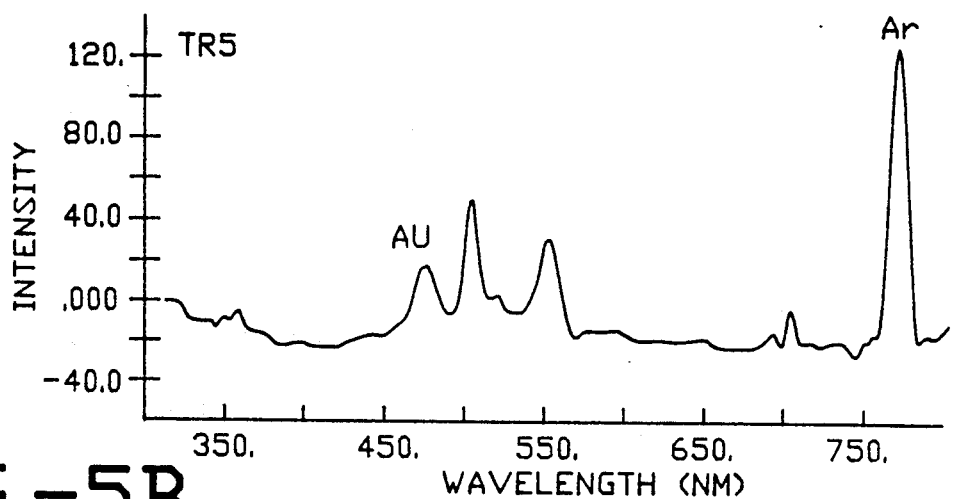
FIG.-5B
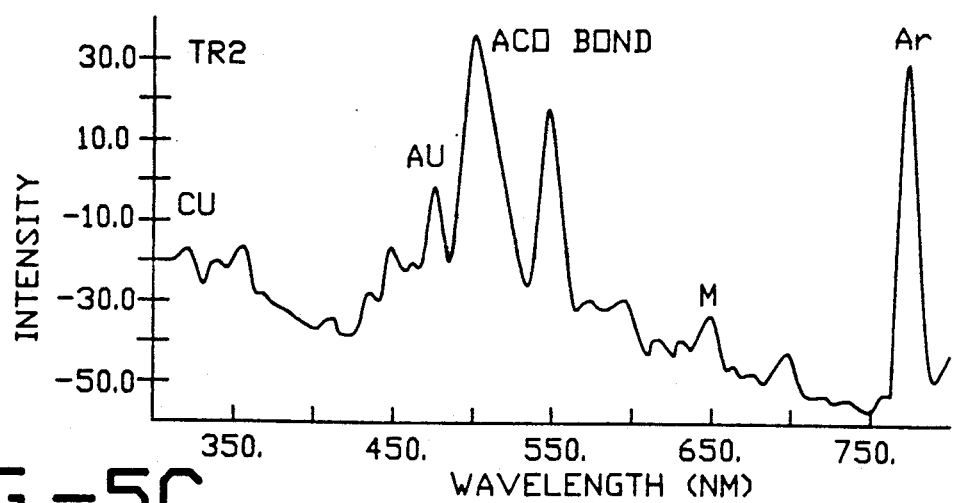
FIG.-5C

APPARATUS AND METHOD FOR AUTOMATICALLY IDENTIFYING CHEMICAL SPECIES WITHIN A PLASMA REACTOR ENVIRONMENT

The present invention relates generally to an apparatus and method for automatically identifying the chemical species found within a plasma reactor chamber during semiconductor wafer manufacturing procedures. More particularly, the invention allows a real time auto-identification of the chemical species detected within the gaseous plasma to facilitate control and/or study the plasma reactor environment during processing.

BACKGROUND OF THE INVENTION

Semiconductor chips are frequently processed within a plasma reactor chamber containing a reactant plasma having a high ionic charge. When the plasma contacts the surface of a wafer to be etched, it assumes a charge that is opposite the plasma's charge. The potential difference between the plasma and the wafer induces an ionic bombardment of the wafer's surface. During normal fabrication procedures, these potentials are high enough to provide sufficient ion bombardment to break chemical bonds and to either sputter away thin layers of the wafer's surface or to deposit a thin layer of surface materials over the wafer. To ensure that the desired etching and/or deposition occurs, it is important to closely control the plasma environment throughout the entire fabrication process. Specifically, the plasma pressure, the ion concentration level and the relative volume(s) of the reactant gases must be closely monitored.

THE PRIOR ART

Traditionally, wafer fabrication processes have been monitored by rigorous attention to parameters such as RF power, gas mixtures and flows, reactor chamber pressure, substrate pressure and wafer loading factors. The interaction of these parameters with respect to the plasma gas phase chemistry is extremely complex, thus making process repeatability difficult and optimization poor.

More recently, optical emission spectroscopy has been utilized to identify and monitor the chemical species in the plasma. In current spectroscopy plasma monitoring systems, a series of real time spectra displays are generated, each of which serves as a snapshot of the chemical constituates of the plasma at the time the spectrum was taken. Each spectrum display takes the form of a graph which plots the intensity of light emitted within the chamber versus wavelength over a designated frequency range. The displays are typically characterized by a multiplicity of spaced apart intensity peaks, with each significant intensity peak corresponding to the presence of a specific chemical species within the plasma. Accordingly, each chemical specie having a significant volume within the plasma, will appear as an intensity peak at the specific wavelength emitted by that species.

To optimize an ongoing wafer fabrication process, an operator photographs or otherwise saves a spectral display at various stages in the fabrication process. For example, this can be done by saving the display on a computer screen. The particular chemicals occurring within the plasma are then identified by visually comparing the intensity peaks within the spectrum display to a set of libraried waveform peaks corresponding to specific individual chemical species that can be expected to be found within the plasma chamber. Once the intensity peaks are identified, the volume or mass of each identified specie can be ascertained from the magnitude of the intensity peak. This also is performed manually by the system operator who must visually compare the intensity peaks of the selected spectral display with a reference spectrum "fingerprint" of the plasma under normal conditions to determine if the species identified are present at the proper volume in the plasma. This monitoring method aids the operator in pinpointing and diagnosing problems within the wafer fabrication process. Spectroscopy can also be utilized to determine the completion or end point of wafer fabrication processes in a similar manner. Examples of such prior art include Savage, Dr. Richard N. and Lettire, Kevin C., "Characterizing Reactive Plasma Chemistries," *Microelectronic Manufacturing and Testing*, (November 1986); UTI Instruments Company, "The Intelligent Way to Control the Environment Inside Your Processes," *ISS-325 Intelligent Sampling Systems*, (Sunnyvale, Calif. 1984); Savage, Richard N., "Applications of Optical Emission Spectroscopy to Semiconductor Processing," *Spectroscopy*, Vol. 2 (No. 8), pp. 40–42, (1987).

The prior art, as described above, has several limitations. In the devices limited to simply generating a spectral plasma display, an experienced operator is required to first visually identify the chemical species within the plasma. This is a tedious and often inaccurate task. The spectral displays generated by various species often appear similar to the human eye, and therefore misidentification occurs frequently. Once identified, the operator must mentally decide if the species is present at an acceptable level and take action accordingly. The identification procedure is often a time consuming task. Failure to rectify problems in real time can lead to the demise of an entire batch of wafers.

In U.S. Pat. No. 4,365,303, issued to Carter et al, a method and apparatus for determining the nature of an unknown substance is disclosed. The apparatus includes a means for entering into a computing apparatus a peak table of the spectrum of an unknown substance. The computing apparatus adjusts the peak table to a standardized format and then compares or matches the peak table of the unknown substance with a library of chemical structural units contained in the memory of the computing apparatus. Thereafter, the apparatus makes a list of the possible chemical structural units most closely corresponding to the unknown substance. In addition, a method for identifying infrared spectra by correlation techniques is disclosed in the research thesis by Linda A. Powell, *Computer Search and Identification of Infrared Spectra by Correlation Techniques*, Indiana University, Bloomington, Ind., 1977.

In U.S. Pat. No. 4,493,745, issued to Chen et al., a method for etching a batch of silicon wafers to end point using optical emission spectroscopy is disclosed. In the preferred embodiment, and in a first alternative embodiment, a computer simulation is performed using an algorithm describing the concentration of the monitored etch species within the etching chamber as a function of time. The simulation produces a time period for continuing the etching process past a detected time while monitoring the intensity of the emission of the etch species. In a second alternative embodiment, this latter time period is calculated using mathematical distributions describing the parameters of the etching process. In all the embodiments, the actual time that the end point of an etching process is reached is closely approximated.

In the two patents cited above, a means for automatically identifying in the chemical species found within a plasma reactor chamber to facilitate the real time control of the plasma environment during semiconductor wafer manufacturing procedures is not disclosed.

SUMMARY OF THE INVENTION

Accordingly, it is a primary objective of the present invention to provide an accurate method and an apparatus for automatically identifying the chemical species in the plasma reactor chamber.

Another object of the invention is to provide a method and apparatus for automatically identifying plasma species utilizing an auto correlation between a plasma spectrum and a library of spectra for identifying plasma chemical species and the volumes thereof.

Another object of the invention is to provide a method and an apparatus for automatically controlling a plasma reactor environment by automatically identifying the abnormal presence of chemical species, pinpointing the source of the abnormal species, and correcting the problem.

To achieve the foregoing and other objects and in accordance with the purpose of the present invention, there is provided a method and apparatus to control the plasma environment in a semiconductor fabrication chamber. The apparatus and method include a means for generating a spectrum indicative of the chemical species within the plasma. An electronic library containing a multiplicity of predefined spectral patterns is also provided. A processor automatically correlates the generated spectrum with the predefined spectra patterns in the library, and yields a correlation value for each intensity peak in the actual spectrum. A subset of the predefined spectral patterns based on the highest correlation values are selected and used to identify the chemical species in the plasma, as well as their respective volumes. A comparator compares the subset with a target set of plasma species and volumes and a controller generates a control signal in response to the comparison to control the chamber environment. In a preferred embodiment, the control signal automatically controls the plasma environment in the reactor chamber when the subset differs from the target set by a predefined amount.

BRIEF DESCRIPTION OF THE DRAWINGS

Additional objects and features of the invention will be more readily apparent from the following detailed description and appended claims when taken in conjunction with the drawings, in which:

FIGS. 3A through 3E pictorially illustrate the auto identification steps executed by the apparatus of FIG. 2 for controlling the reactor chamber environment according to the present invention.

FIG. 4 shows a plasma reactor containing a gold target having a copper support block containing a gold inlay during a sputtering procedure.

FIGS. 5A and 5B are model fingerprint spectra taken at key times during a sputtering procedure and FIG. 5C is a sample spectra of an actual sputtering procedure taking place in the reactor shown in FIG. 4.

DESCRIPTION OF THE PREFERRED EMBODIMENT

Figure 1:
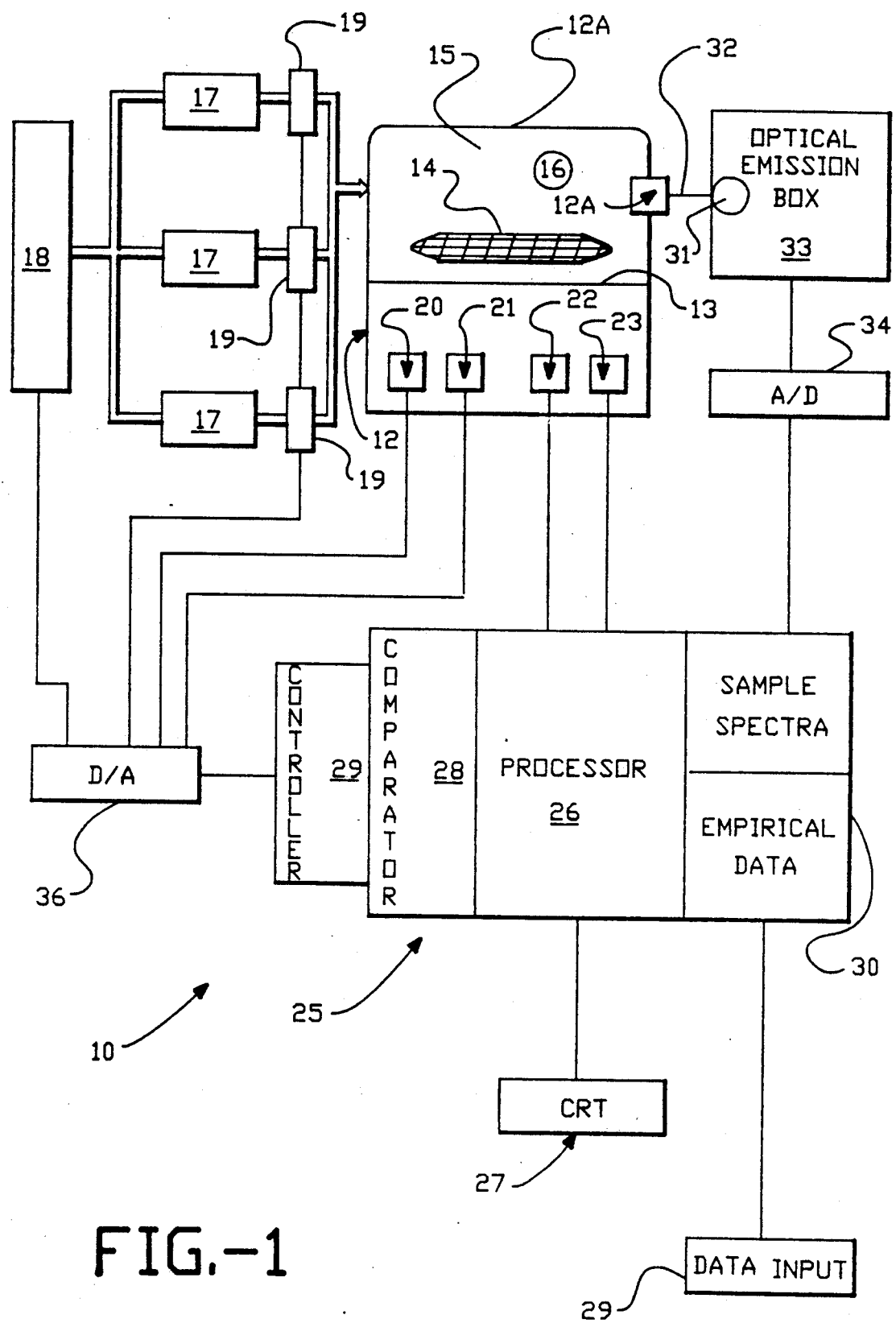
FIG. 1 is a block diagram of a system for controlling the environment in a plasma reactor chamber according to the present invention.

Reference is initially made to FIG. 1 which shows a block diagram of a system suitable for controlling the environment of a plasma reactor chamber 12 in accordance with the present invention. The reactor chamber 12 is a vacuum assembly capable of withstanding the gas pressures typically used during wafer fabrication procedures. A platform 13 within the chamber forms a surface upon which a wafer 14 rests during fabrication processes. A window 12a within the chamber 12 is optically transparent to permit light to emit from the chamber.

A gaseous plasma 15, comprising a plurality of chemical species 16, is contained within the chamber 12. The various chemicals used during processing are maintained within storage tanks 17. Each storage facility 17 is coupled to the plasma chamber 12 by appropriate ducting. The flow of gases from a particular storage tank 17 into the chamber is controlled by the pump 18 and valves 19 that are associated with each of the storage tanks. A pressure regulator 20 is provided to maintain the desired plasma pressures and to exhaust container gases at the appropriate stages in the fabrication process. A pressure sensor 22 disposed within the chamber is adapted to sense plasma pressure and to generate a pressure signal.

A control system 25, including a processor 26, a CRT 27, a comparator 28, a controller 29 and memory 30 are utilized to monitor and control the plasma environment within chamber 12. It will be appreciated by those skilled in the art that the comparator 28 and controller 29 may be included in the processor 28 and implemented with software.

The processor 26 is electrically connected to receive the pressure signal. The processor 26 controls the chamber pressure and the volumes of particular chemical species 16 in the plasma 15 by regulating the delivery of the various chemicals stored within storage tanks 17 to the chamber and regulating the discharge of gases from the chamber through pressure regulator 20. To increase the volume of a particular chemical specie 16 within the plasma, the processor 26 electronically activates the valve 19 and pump 18 associated with the storage tank 17 holding the desired chemical. To decrease the plasma pressure, the processor controls the opening of the pressure regulator 20 to allow plasma gas to escape from chamber 15. Thus, any time an over-pressurization occurs, or a particular step in the processing is completed, the processor may open the pressure regulator 20 to permit gases to escape from chamber 12.

A power meter 23 adapted to sense the plasma ion concentration level and to generate a plasma power or ion level signal, is electrically connected to the processor 26 and continuously informs the processor of the ion concentration level. In response to the power meter 23, the processor 26 regulates the output of power regulator 21 to increase or decrease the ion concentration level of the plasma 15 by varying the power supplied to the power regulator 21 which regulates the strength of the electric field within the chamber.

The processor memory 30 is arranged to store empirical data that is useful in determining the composition of gases within the chamber 12 and for wafer processing control. Generally, four types of empirical data are stored. First, a sequence of model spectral patterns or "fingerprints" taken at key times during normal wafer fabrication and processes, including the intensity of individual species 16 and hence specie ion levels at key stages in the process. Second, a target set of data values. The target values define a deviation range for informing the processor if the detected species intensities, plasma pressure and ion levels deviate from the model "fingerprint" spectra beyond an acceptable range. Third, fabrication process parameters for the processor to rely on to control wafer fabrication procedures. For example, the target plasma power, gases and pressure levels, the rates of change for unacceptable contaminant species and acceptable process species. Fourth, a library containing a multiplicity of predefined spectral patterns. Each library spectra is used to identify a specific chemical specie within the plasma. By way of example, a suitable library for present wafer processing systems may contain 60 spectra patterns indicative of the specific wavelengths emitted by 60 individual chemicals found in plasma reactor chambers during wafer processing. The spectral patterns are typically limited between a minimum wavelength of 200 and a maximum wavelength of 1,000 nanometers. However, it should be appreciated that the actual range of the library spectral patterns may be widely varied, so long as they permit accurate identification of the chemicals within the plasma chamber 12.

An optical cable 32 is optically positioned near the chamber window 62a and is adapted to receive the plasma light intensity signals after they pass through the window. The cable 32 transfers the light signals to optical emission box 33. The photosensor 31 generates an analog signal that is directly proportional to the light intensity for each wavelength. In the preferred embodiment, a spectrum ranging from 200 to 1,000 nanometers is sufficient to provide information to control the plasma reactor environment based on current processing technologies. In the future, it is believed a spectrum ranging from 100 nanometers to 2,000 nanometers will be necessary to detect and identify the species contained in reactor chambers during wafer processing.

Generally, the light intensity signal must exceed a minimum threshold value for the emission box 33 to generate an analog signal indicating a measurable light intensity at a particular wavelength. For light intensity signals falling below the threshold value, the emission box generates an analog signal indicating that light intensity at the particular wavelength is substantially non-existent. The optical emission box 33 also normalizes the analog signals to compensate for variations in the gain of photosensor 31. An analog-to-digital (A/D) convertor 34 is electrically connected to the output of the optical emission box 33. The A/D convertor 34 samples the emission box 33 analog signals and converts each analog sample into a digitized sample spectrum for data processing. The control system 25 is electrically connected to receive the sampled digitized spectrum signals and to store them in the processor's memory 30. The actual sample rates may vary, but must be fast enough to provide on-line control of the wafer processing. By way of example, current wafer fabrication technology, requires sampling rates of approximately 1 sample/second. In the future, it is believed that sampling rates in the vicinity of 100 samples/second will be necessary to accommodate advances in wafer manufacture processes.

Figure 2:
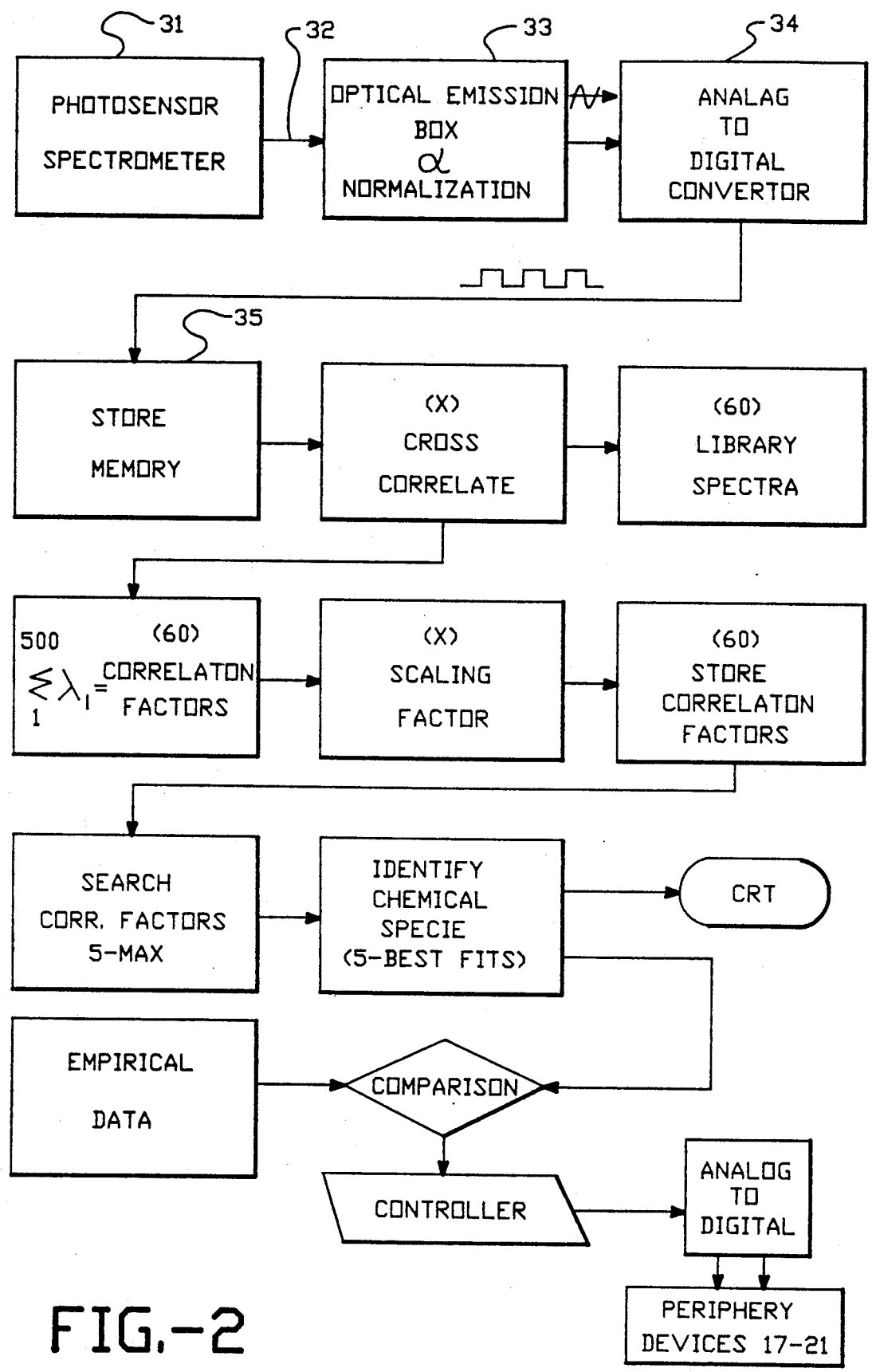
FIG. 2 is a flow diagram showing the steps of the auto-identification performed by the system in FIG. 1.

The process for automatically identifying the species or chemical composition in the plasma will be described with reference to the flow chart shown in FIG. 2 and the apparatus shown in FIG. 1. The processor performs an automatic cross correlation between each of the multiplicity of predefined libraried spectra and the actual measured spectrum of each sample. A scaling factor is applied to compensate for the multiplicity of wavelengths that each chemical specie 16 emits after each correlation has been performed. A list of the libraried species yielding the highest correlation values are used to identify the species and intensities thereof in the plasma. In the described embodiment, the list consists of five possible species identifiers for each plasma spectra. The real time spectrum of the ongoing plasma reaction and the five possible specie identifiers along with their correlation values are displayed on the CRT for the system operator. Such information facilitates operator study of the ongoing fabrication process. Furthermore, the comparator 28 compares the identified species and their respective intensities detected in the plasma with the empirical data or fingerprint spectral patterns. If the comparison falls within the expected target range, the system operator is informed that no apparent problems have developed in the process.

Alternately, the operator may program the control system 25 to automatically control the plasma reactor environment during processing. If the comparator yields a deviation beyond the target range, the processor 26 instructs the controller 29 to generate a digital control signal to adjust the chamber 12 environment. A digital-to-analog converter 36 (D/A) connected to the output of the controller, converts the control signal to analog form to regulate the reactor environment by manipulating the chamber periphery devices 18–21 to correct the deviation. For example, if the intensity (and thus the concentration) of carbonmonoxide (CO) during an etch procedure is detected lower than the acceptable range as defined by the target values, the processor 26, relying on the empirical data, determines that the most likely causes of the deficiency are: (1) an insufficient volume of oxygen within the chamber; (2) insufficient volume of carbon in the plasma; or (3) an insufficient ion concentration within the plasma. Thereafter, the processor performs an oxygen level, a carbon level, and an ion ion level comparison with the target value for these parameters to determine which of the postulated problems is deviating from the target values beyond the acceptable range. Depending on the outcome, the control signal directs the pump 18 and the appropriate valve 19 to introduce more oxygen or carbon into the chamber 12, or increase the output of power regulator 21, or a combination thereof.

Referring now to FIG. 3, a pictorial representation of the species auto-identification process is shown. In a Master of Science thesis entitled, COMPUTER SEARCH AND IDENTIFICATION OF INFRARED SPECTRA BY CORRELATION TECHNIQUES, presented by Linda Powell in August, 1977 to Indiana University, Bloomington, Ind., which is incorporated herein by reference, fundamental principles of the correlation technique utilized by the present invention is taught. In summary, the sample spectra is cross correlated with each of the library spectra and the "best fit" is determined from the outcome of the correlation. In the preferred embodiment, the processor executes the equation below to automate the species identification technique:

$$C_{ab}(n\Delta t) = \frac{1}{T} \sum_{t=0}^{T} a(t)\, b(t \pm n\Delta t) \quad n = 200, 201 \ldots 1000$$

where
- $t = 500$ data points
- $t = 1$ data point,
- $a(t)$ = actual spectrum, and
- $b(t \pm n\Delta t)$ = library spectra.

The auto-identification technique is performed for each library spectra to identify all the species potentially present within the plasma 15.

To visualize how the cross correlation auto-identifies a species in the plasma, the example illustrated in FIGS. 3A through 3D is provided. A library spectra of hydrogen, having an intensity wavelength between 400 to 500 nanometers is shown in FIG. 3A. The remainder of the waveform, where no peaks exist, is assigned an intensity value of approximately one. Note, in the wavelength range between 200 and 1000 nanometers selected for the preferred embodiment, the library spectra typically contain multiple peaks. In FIG. 3B, an actual spectral sample of the plasma 15 having a number of peaks at different wavelengths between 400 and 500 nanometers is shown. Note the existence of a peak between 400 to 450 nanometers.

During cross correlation, the amplitudes of the two waveforms between the selected range of 300 to 800 nanometers, are multiplied. FIG. 3C shows the spectral waveform which represent the product of the multiplication between the actual sample spectrum and the library spectrum. An enhanced peak exists at the bandwidth of 400 to 500 nanometers, where the library spectra and the actual spectrum have a common peak. In contrast, where the library spectra has no peak in common with the actual data spectrum, the product of the multiplication results in peaks with amplitudes equal to those of the actual spectrum in FIG. 3B.

The actual spectral waveform of FIG. 3E which is equal to 3B is subtracted from product waveform of FIG. 3C in the next auto-identification step. The subtraction removes from the waveform of FIG. 3C any peaks not in common with the library waveform of FIG. 3A. The resulting waveform, as illustrated in FIG. 3D, provides a peak only where the libraried spectrum of FIG. 3A has a peak, thereby identifying the presence of the libraried specie in the actual plasma sample.

The peaks in FIG. 3D have two important characteristics. First, the area under the resulting waveform or the correlation factor determines the degree of accuracy of the auto-correlation technique. A large area under the curve signifies a "best fit" and therefore a high degree of identification accuracy. Generally, a correlation factor in the range of 90% to 99% is considered highly accurate. A correlation factor between 80% and 89% is considered mediocre, and anything less than 80% is considered an inaccurate identification. The second characteristic to be analyzed is the amplitude of the resulting peak of FIG. 3D. Generally, the amplitude of the peak signifies the relative abundance of the species at the time the sample was taken.

Referring to a specific example illustrated in FIG. 4, the automatic control of a sputtering procedure carried out in accordance with the present invention will be described. A chamber 12 adapted to perform the sputtering of a precious metal onto a masked wafer 14 is shown. Within the chamber 12, a solid copper (Cu) mass 50 containing a gold (Au) inlay 51 is physically positioned above the wafer 14. The gold 51 is disposed over the copper in a thin layer so that no portion of the copper is exposed to the plasma 15. The plasma contains a high concentration of the reactant gas argon (Ar). During the sputtering procedure, argon ions bombard the gold inlay 51, causing the gold molecules to sputter away from the copper mass 50 and to fall onto the masked wafer 14. Once the gold has been sputtered, the copper mass itself is exposed to the argon gas, which induces copper sputtering. At this point the gold sputtering process is complete and the argon gas should immediately be discharged from the chamber 12 to prevent significant sputtering of the copper, which is undesirable.

Referring now to FIGS. 5A through 5C, a number of spectral waveforms to illustrate system 10 control of the sputtering in the chamber of FIG. 4 are shown. FIG. 5A shows the "fingerprint" spectra in a reactor 12 using an argon based plasma before any gold has been sputtered. The spectral waveform is noted by high intensity spike at approximately 750 nm which corresponds to the argon gas. There is no intensity spike at 479 nm, which would indicate the presence of gold. FIG. 5B shows the spectral fingerprint of the chamber during normal sputtering procedures. It is characterized by an argon intensity spike which remains substantially unchanged, while the intensity spike characteristic of gold has increased indicating that gold is present in the plasma 15 due to sputtering.

Referring now to FIG. 5C, an actual spectral waveform is shown after portions of the gold layer has been completely sputtered away exposing the copper to the argon plasma. As a result, copper sputtering has started to occur and is detectable by traces of copper in the plasma. Relying on the auto-identification technique described above, the processor detects the presence of an intensity spike characteristic of copper. The comparator compares the actual spectrum of FIG. 5C with the fingerprint spectrum of FIG. 5B, and determines that the presence of Cu is outside the target range of values.

Relying on the third type of empirical data for sputtering procedures, the processor acknowledges that the detection of copper is due to the fact that portions of the gold layer have been completely removed from the copper mass 50, exposing copper to the argon ion bombardment. Thereafter, the processor instructs the controller to generate control signals to automatically stop the sputtering procedure based on the auto-identification of copper in the plasma 15. The control signals direct the reduction of the plasma ion intensity level, and depressurize the chamber by opening pressure regulator 20 to permit the argon gas to escape.

The auto-identification technique of the present invention can also be used for end point detection of an etching process. Such end point detection requires that a specific emitting species be identified and that its spectral features change intensity in a detectable fashion when the interface between the film and the substrate is reached. It will be obvious to those skilled in the art that both the reactant and the product species may be used for end point detection.

Figure 6A:
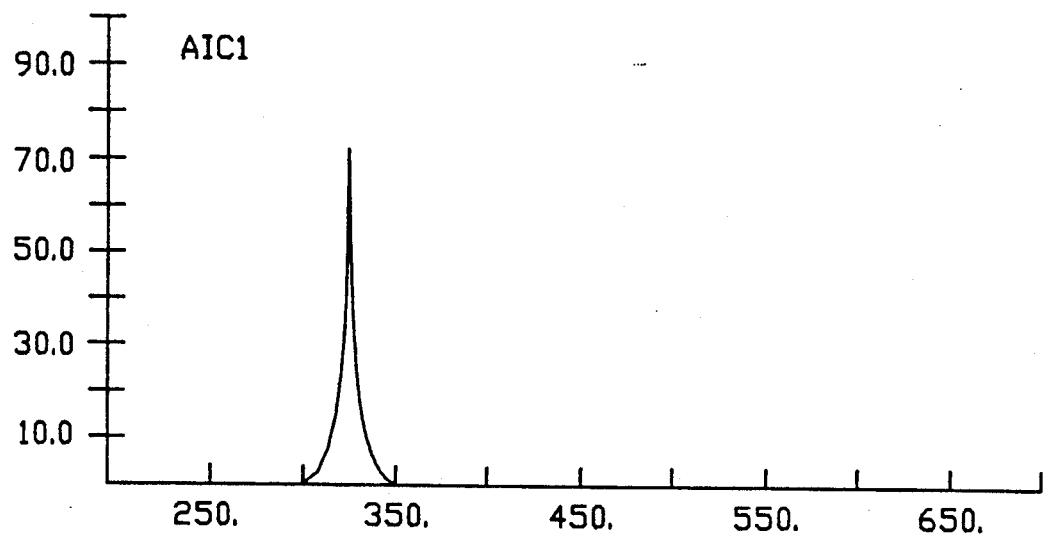
FIG. 6A is a graph showing the identification and intensity of aluminum chloride product gas during an etch procedure, and FIG. 6B plots the intensity of the aluminum chloride gas from beginning to end point and is used for end point detection of an aluminum etch procedure.
Figure 6B:
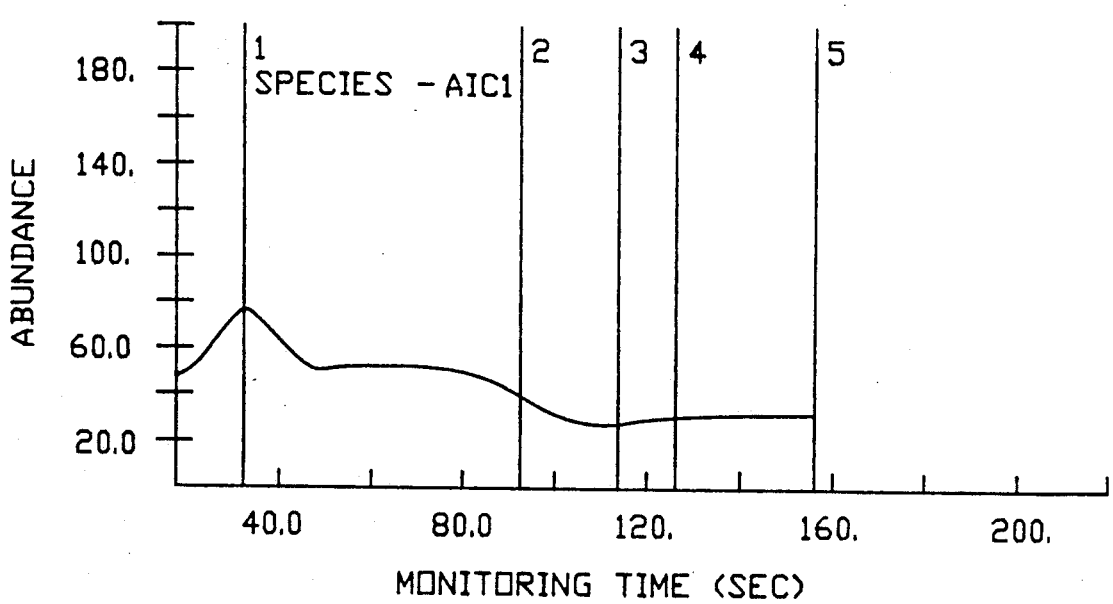

Referring now to FIGS. 6A and 6B, two graphs are shown to illustrate end point detection of an aluminum (Al) using a chlorine (Cl) based plasma reactant are shown. During the etching procedure, the aluminum (Al) and the chlorine reactant chemical combine to form an aluminum chloride (AlCL) product gas. In FIG. 6A, a spectrum displaying the identification and intensity of aluminum chloride gas between 300 and 350 nanometers is shown.

In FIG. 6B, the intensity of the identified aluminum chloride gas of FIG. 6A is plotted from beginning to end point. The processor uses two characteristics of the waveform for end point detection. First, the sharp fall in relative intensity at 100 seconds into etching, indicating that the removal of the aluminum film is substantially complete and therefore little aluminum is available to form the aluminum chloride product gas. The second indicator of end point detection is an increase of the percentage of change of aluminum chloride intensity over time or the change in the slope of the waveform of FIG. 6B. To control endpoint detection, the operator is required to store in the processor's memory 30 the relative intensity threshold for aluminum chloride and change in the slope value indicating end point. The waveform of FIG. 6B is constructed by the processor by identifying and determining the relative intensity of aluminum chloride gas in the plasma at each sampling interval using the auto-correlation technique described above. The processor then plots the intensity at each sampling interval as a function of time between beginning and end point. To control end point detection, the comparator compares the actual aluminum chloride waveform's intensity and change in slope at each sampling interval. When the threshold values are reached, the controller generates a control signal to stop the etch procedure by regulating the power regulator 21 to reduce the plasma ion level, a control signal to open the pressure regulator 20 to allow the chlorine based plasma gas to escape from the chamber, and a control signal to prevent chlorine gas to enter into the chamber, or any combination thereof.

Accurate endpoint determination can provide both an improved yield and quality of integrated circuits. The etch rate can increase significantly at end point, because the exposed area decreases to a minimum while the etching concentration approaches a maximum. Terminating the etch promptly at end point reduces undercutting of the etch mask, thus reducing damage to the wafer under fabrication. Furthermore, if the etch can be terminated in a timely manner, the etching system and the chemical and molecular species 16 it consumes are utilized more efficiently.

While the present invention has been described with reference to a few specific wafer etching embodiments, the description is illustrative of the invention and is not to be construed as limiting the invention. Various modifications and other wafer manufacture applications may occur to those skilled in the art without departing from the true spirit and scope of the invention as defined by the appended claims. For example, the specie auto-identification technique of the present invention may also be utilized in other wafer fabrication or thin-film processes, including, but not limited to photoresist stripping, ion-milling, reactive sputtering, plasma enhanced chemical vapor deposition and photolithographic techniques.

What is claimed is:

1. In a method to control the environment of a plasma chamber containing at least one chemical species during a semiconductor fabrication procedure, comprising the steps of:
   generating a sample spectrum indicative of the chemical species in the plasma;
   providing a library containing a multiplicity of predefined spectral patterns, each spectral pattern being indicative of a particular chemical species;
   automatically correlating said spectrum with said predefined spectral patterns in said library, and yielding a correlation value for each libraried spectrum pattern;
   identifying the chemical species in the plasma based on the highest correlation values, and generating an identifier list indicating the chemical species and abundances thereof in the plasma.

2. The method of claim 1, wherein said library of said predefined spectral patterns range from a minimum spectrum wavelength of 100 to maximum spectrum wavelength of 2000 nanometers, and said step of generating a spectrum indicative of the chemical species in the plasma is performed at a sampling rate of at least one hundred samples per second.

3. The method of claim 1, wherein said step of automatically correlating said spectrum with said predefined spectral patterns in said library is performed at a rate of at least one hundred samples per second.

4. The method of claim 1, wherein each said automatic correlation step includes the steps of:
   generating a product spectrum by multiplying the amplitude of a selected library spectrum and the actual sample spectrum within a selected wavelength range; and
   subtracting said actual sample spectrum from said product spectrum, wherein the presence of a peak in the resulting spectral waveform identifies the presence of the chemical species associated with the library spectrum in the actual plasma sample.

5. The method of claim 4, wherein the area under said resultant peak indicates the degree of accuracy of said correlation species identification step, and the amplitude of said resultant peak indicates the relative abundance of the species at the time the sample was taken.

6. The method of claim 1 further comprising the step of comparing said identified species and abundances with a target set of plasma species and abundances and determining the deviation of the identified species from said target.

7. The method of claim 6, further comprising the step of generating a control signal when said comparison yields a result greater than a predetermined deviation value, said control signal controlling the chamber environment.

8. The method of claim 7, wherein said control signal is adapted to control the chamber environment by regulating the plasma pressure, the abundances of particular chemical species in the plasma, and the ion level within the plasma.

9. In a method to control the environment of a processing chamber containing at least one chemical species comprising the steps of:
   generating a sample spectrum indicative of the chemical species in the plasma;
   providing a library containing a multiplicity of predefined spectral patterns, each spectral pattern being indicative of a particular chemical species;

automatically correlating said spectrum with said predefined spectral patterns in said library, and yielding a correlation value for each libraried spectrum pattern;

identifying the chemical species in the plasma based upon the highest correlation values, and generating an identifier list indicating the chemical species and abundances thereof in the plasma; and comparing said identified species and volumes with a target set of plasma species and volumes and determining the deviation of the identified species from said target.

10. The method of claim 9, further comprising the step of generating a control signal when said comparison yields a result greater than a predetermined deviation value, said control signal controlling the chamber environment.

11. The method of claim 9, further comprising the step of controlling the chamber environment when said subset differs from said target set by a predefined deviation range.

12. In an apparatus to control the plasma environment in a semiconductor fabrication chamber containing at least one chemical species, comprising:

a means for generating a sample spectrum indicative of the chemical species in the plasma;

a means for providing a library containing a multiplicity of predefined spectral patterns, each spectral pattern being indicative of a particular chemical species;

a means for automatically correlating said spectrum with said predefined spectra patterns in said library, and yeilding a correlation value for each libraried spectrum pattern;

a means for identifying the chemical species in the plasma based upon the highest correlation values, and generating an identifier list indicating the chemical species and volumes thereof in the plasma.

13. The apparatus of claim 12, further comprising means for controlling the plasma in the semiconductor chamber when said subset differs from said target set by a predefined deviation range.

14. In an apparatus to automate the control of the plasma environment in a semiconductor fabrication chamber containing at least one chemical species using spectroscopy to identify chemical and molecular species to a high degree of accuracy in the chamber, comprising:

a means for generating a sample spectrum of the chemical species in the plasma;

a means for providing a library containing a multiplicity of predefined spectral patterns;

a processing for receiving said spectrum of intensity signals, said processor automatically correlating said sample spectrum with said multiplicity of predefined library spectra, and identifying the chemical species and abundances in the chamber plasma based on said correlation.

15. The apparatus of claim 14 further comprising a pressure sensor adapted to sense chamber pressure and to generate a pressure signal; and a power meter adapted to sense chamber ion level and to generate an ion level signal; wherein said processor is adapted to receive said pressure signal and said ion level signal.

16. The apparatus of claim 15, wherein said processor is adapted to compare said identified chemical species and abundances with a target set of chemical species and abundances, to compare said plasma pressure signal to a target pressure value and to compare said plasma ion level signal to a target ion level value.

17. The apparatus of claim 16, wherein said apparatus further includes a number of chamber periphery devices to control the plasma environment in the chamber, including a means for introducing chemical species gases into the chamber, a means to regulate plasma ion concentration levels and a means to exhaust plasma gases from the chamber.

18. The apparatus of claim 17, further including a controller electrically adapted to respond to said comparator, said controller generating a control signal to control said periphery devices if said comparisons deviate beyond said target values.

19. The apparatus of claim 18, wherein said processor, said comparator and said controller are controlled by a control system software program, and said library of said predefined library spectra and said target values are stored in processor memory.

* * * * *